United States Patent [19]

Maruyama et al.

[11] 4,017,624
[45] Apr. 12, 1977

[54] N-(ω-AMINO)ALKYLANILINE DERIVATIVES

[75] Inventors: Isamu Maruyama, Minoo; Masaru Nakao, Osaka; Kikuo Sasajima, Toyonaka; Shigeho Inaba, Takarazuka; Hisao Yamamoto, Nishinomiya, all of Japan.

[73] Assignee: Sumitomo Chemical Company, Limited, Osaka, Japan

[22] Filed: Aug. 8, 1975

[21] Appl. No.: 603,240

Related U.S. Application Data

[62] Division of Ser. No. 439,827, Feb. 5, 1974, Pat. No. 3,917,598.

[30] Foreign Application Priority Data

Feb. 5, 1973 Japan ............................. 48-15025

[52] U.S. Cl. ............................. 424/250; 260/293.6; 260/293.66; 260/293.79; 424/267
[51] Int. Cl.$^2$ ......................................... C07D 401/04
[58] Field of Search ..... 260/293.6, 293.66, 293.79; 424/250, 267

[56] References Cited

UNITED STATES PATENTS 3,922,266  11/1975  Katsube et al. ................ 260/240 J
3,925,387  12/1975  Maruyama et al. ......... 260/268 PH

*Primary Examiner*—G. Thomas Todd
*Attorney, Agent, or Firm*—Birch, Stewart, Kolasch and Birch

[57] ABSTRACT

An N-(ω-amino)alkylaniline derivative of the formula:

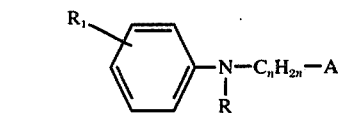

and its pharmaceutically acceptable salts, which are useful as neuroleptic agents and can be prepared by reacting a compound of the formula:

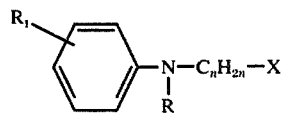

with a compound of the formula:

H—A

[wherein R is hydrogen, $C_1$–$C_7$ alkyl, $C_1$–$C_7$ alkanoyl or aroyl, $R_1$ is hydrogen, halogen, $C_1$–$C_7$ alkyl or $C_1$–$C_7$ alkoxy, A is

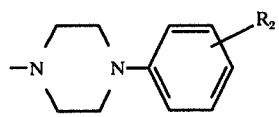

(wherein $R_2$ is hydrogen, halogen, $C_1$–$C_7$ alkyl, $C_1$–$C_7$ alkoxy or trifluoromethyl),

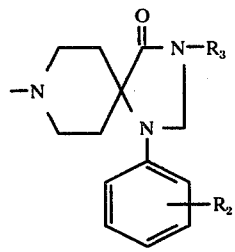

(wherein $R_2$ is as defined above and $R_3$ is hydrogen, $C_1$–$C_7$ alkyl or $C_1$–$C_7$ alkanoyl),

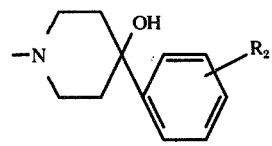

(wherein $R_2$ is as defined above or

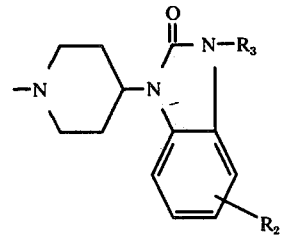

(wherein $R_2$ and $R_3$ are each as defined above) and $n$ is 2, 3 or 4].

10 Claims, No Drawings

N-(ω-AMINO)ALKYLANILINE DERIVATIVES

This is a divisional of copending application Ser No. 439,827, filed on Feb. 5, 1974, now U.S. Pat. No. 3,917,598.

The present invention relates to novel N-(ω-amino)-alkylaniline derivatives, and their preparation and use. More particularly, it relates to novel N-(ω-amino)alkylaniline derivatives represented by the formula:

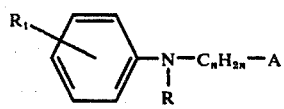

wherein R is hydrogen, $C_1$–$C_7$ alkyl, $C_1$–$C_7$ alkanoyl or aroyl, $R_1$ is hydrogen, halogen, $C_1$–$C_7$ alkyl or $C_1$–$C_7$ alkoxy, A is

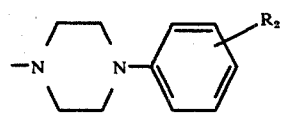

(wherein $R_2$ is hydrogen, halogen, $C_1$–$C_7$ alkyl, $C_1$–$C_7$ alkoxy or trifluoromethyl),

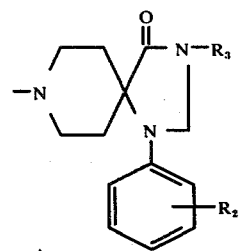

(wherein $R_2$ is as defined above and $R_3$ is hydrogen, $C_1$–$C_7$ alkyl or $C_1$–$C_7$ alkanoyl),

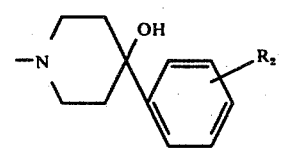

(wherein $R_2$ is as defined above), or

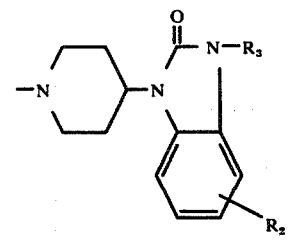

(wherein $R_2$ and $R_3$ are each as defined above) and $n$ is 2, 3 or 4, and their pharmaceutically acceptable salts, pharmaceutical compositions comprising them with pharmaceutically acceptable carriers, and processes for preparing them.

As used herein, the terms "$C_1$–$C_7$ alkyl", "$C_1$–$C_7$ alkoxy" and "$C_1$–$C_7$ alkanoyl" mean such groups containing from one to seven carbon atoms which can be either straight or branched. Thus, the $C_1$–$C_7$ alkyl group represents, for example, methyl, ethyl, n-propyl, isopropyl, n-butyl, isobutyl, n-hexyl and the like; the $C_1$–$C_7$ alkoxy group represents, for example, methoxy, ethoxy, n-propoxy, isopropoxy, n-butoxy, isobutoxy, sec.-butoxy, n-pentoxy and the like; and the $C_1$–$C_7$ alkanoyl group represents, for example, formyl, acetyl, propionyl, n-butyryl, 6-methylhexanoyl and the like. The term "halogen" includes all four halogens, i.e., iodine, bromine, chlorine and fluorine. The term "aroyl" means, for example, benzoyl, halobenzoyl, nicotinoyl and the like.

The group of the formula: $-C_nH_{2n}-$ represents a straight chain or branched chain alkylene group having up to 4 carbon atoms and includes, for example, ethylene, trimethylene, 1-methyltrimethylene, 2-methyltrimethylene and tetramethylene.

The N-(ω-amino)alkylaniline derivatives [I] form pharmaceutically acceptable salts with a variety of inorganic and organic acids such as sulfuric, phosphoric, hydrochloric, hydrobromic, nitric, oxalic, malonic, succinic, lactic, tartaric, maleic, fumaric, formic, acetic, salicylic and p-toluenesulfonic acids.

The preferable class of the N-(ω-amino)alkylaniline derivative [I] is the compound of the formula:

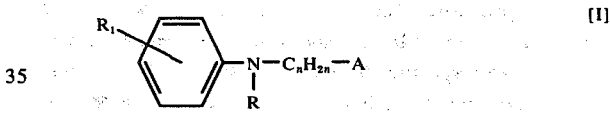

wherein $n$, R and $R_1$ are as defined above and A is

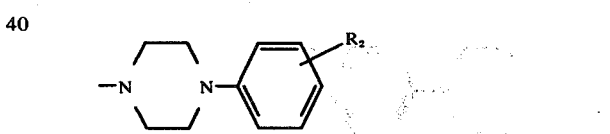

(wherein $R_2$ is as defined above) or

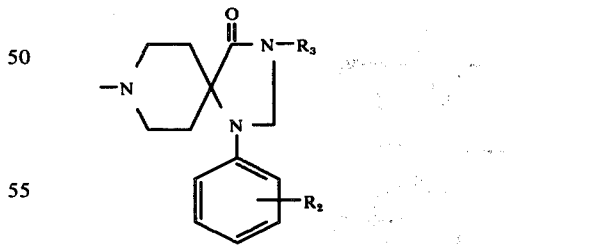

(wherein $R_2$ and $R_3$ are each defined above), and its pharmaceutically acceptable salts. The particularly preferable class is the compound of the formula:

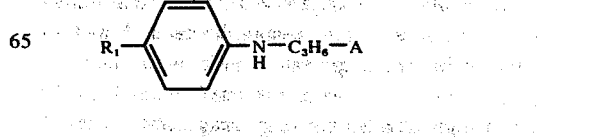

wherein $R_1$ is fluorine, methyl or methoxy and A is

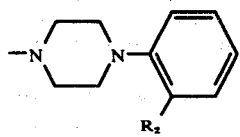

(wherein $R_2$ is $C_1$–$C_3$ alkoxy) or

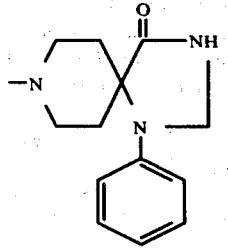

and its pharmaceutically acceptable salts. But, these classes do not limit the present invention.

As the result of the extensive study seeking excellent neuroleptic agents, it has been found that novel N-(ω-amino)-alkylaniline derivatives [I] show a depressant effect on the central nervous system and are useful as neuroleptic agents.

The depressant effect on the central nervous system can be determined by a conventional test method. For instance, anti-apomorphine test establishes the remarkable excellence of the N-(ω-amino)alkylaniline derivative [I] wherein $n$, R and $R_1$ are each as defined above and A is

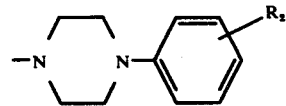

(wherein $R_2$ is as defined above) or

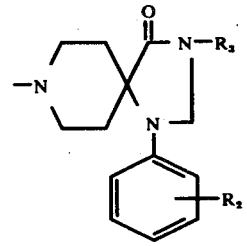

(wherein $R_2$ and $R_3$ are each as defined above), and its pharmaceutically acceptable salts.

The N-(ω-amino)alkylaniline derivatives [I] and their pharmaceutically acceptable salts can be administered orally in conventional dosage forms such as tablet, capsule, solution, suspension, elixir or the like.

A typical tablet may be constituted from 1 to 20 percent by weight of a binder (e.g., tragacanth), from 1 to 20 percent by weight of a lubricant (e.g., talcum, magnesium stearate), an average dose of the active ingredient and q.s. 100 percent by weight of a filler (e.g., lactose). The usual oral dosage is 1 to 1000 mg per day.

Accordingly, a basic object of the present invention is to provide novel N-(ω-amino)alkylaninline [I] and their pharmaceutically acceptable salts which have excellent pharmacological properties. Another object of this invention is to provide processes for producing such novel and useful N-(ω-amino)alkylaniline derivatives [I] and their salts. A further object of the invention is to provide pharmaceutical compositions comprising such novel and useful N-(ω-amino)alkylaniline derivatives [I] or their salts. These and other objects of the invention will be apparent from the following descriptions.

According to the present invention, the novel N-(ω-amino)alkylaniline derivatives [I] can be prepared by reacting a compound of the formula:

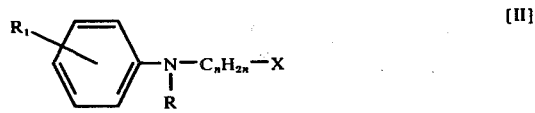

[II]

wherein R, $R_1$ and $n$ are each as defined above and X is halogen (preferably chlorine, bormine or iodine) with a compound of the formula:

$$H-A \qquad [III]$$

wherein A is as defined above.

The reaction may be carried out in the absence or presence of an acid acceptor in an inert organic solvent (e.g., benzene, toluene, xylene, dimethylformamide, pyridine, methanol, ethanol) at a temperature from about room temperature to the boiling temperature of the solvent used. Suitable acid acceptors include sodium carbonate, potassium carbonate, sodium bicarbonate, potassium bicarbonate, sodium hydroxide, potassium hydroxide, sodium hydride, potassium hydride, triethylamine, etc.

The N-(ω-amino)alkylaniline derivatives [I], wherein R is hydrogen, can be also prepared by reducing a compound of the formula:

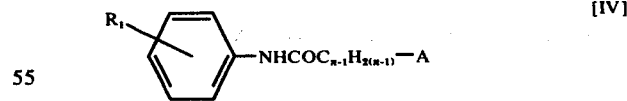

[IV]

wherein $R_1$, A and $n$ are each as defined above with a reducing agent such as lithium aluminum hydride.

The reduction may be carried out at a cooling temperature, room temperature or an elevated temperature in the presence of a solvent or solvent mixture. Examples of the suitable solvent include ether, tetrahydrofuran, dioxane, N-ethylmorpholine and the like.

The compound [IV] can be easily prepared in a conventional procedure according to the following reaction scheme:

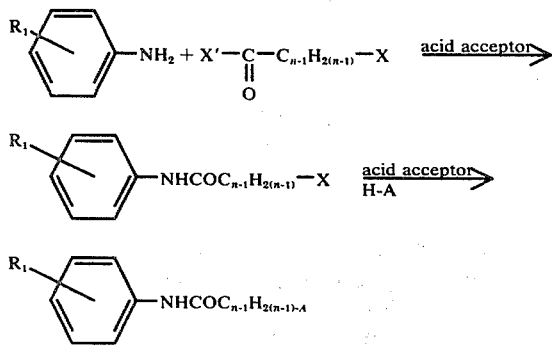

wherein $R_1$, A, $n$, X' are each as defined above.

The present invention is further disclosed in the following examples of more preferred embodiments thereof, which are presented for the purpose of illustration and it is not intended to limit the scope of the invention.

EXAMPLE 1

A mixture of 1.9 g of N-(3-chloropropyl)-p-fluoroaniline, 1.9 g of 1-(o-methoxyphenyl)piperazine, 0.5 g of sodium carbonate and 50 ml of dimethylformamide was heated at 80°–90° C for 15 hours. After cooling, the reaction mixture was poured into water and extracted with benzene. The extract was washed with water, dried over sodium sulfate and evaporated under reduced pressure to give 1-{3-(p-fluoroanilino)propyl}-4-(o-methoxyphenyl)piperazine, m.p. 79°–80° C; recrystallized from cyclohexane, m.p. 84°–84.5° C.

The following compounds were obtained in the same manner as above:

1-{3-(p-Fluoroanilino)propyl}-4-(o-ethoxyphenyl)-piperazine; m.p. 101°–101.5° C;
1-{3-(p-Fluoroanilino)propyl}-4-(o-n-propoxyphenyl)-piperazine, m.p. 76°–77° C;
1-{3-(p-Fluoroanilino)propyl}-4-(o-isopropoxyphenyl)-piperazine, m.p. 79°–80° C;
1-{3-(p-Toluidino)propyl}-4-(o-methoxyphenyl)piperazine, m.p. 72°–73° C;
1-{3-(p-Ethylanilino)propyl}-4-(o-ethoxyphenyl)-piperazine dihydrochloride, m.p. 98°–99° C (decomposition);
1-{3-(p-Anisidino)propyl}-4-(o-methoxyphenyl)-piperazine, m.p. 82°–82.5° C;
1-{3-(p-Fluoroanilino)propyl}-4-(o-chlorophenyl)-piperazine dihydrochloride, m.p. >240° C;
1-{3-(p-Fluoroanilino)propyl}-4-(o-tolyl)piperazine dihydrochloride, m.p. >240° C;
1-{3-(p-Chloroanilino)propyl}-4-(o-ethoxyphenyl)-piperazine, m.p. 90°–91° C;
1-{2-(p-Fluoroanilino)ethyl}-4-(o-methoxyphenyl)-piperazine dihydrochloride, m.p. 199°–200° C (decomposition);
1-{4-(p-Fluoroanilino)butyl}-4-(o-methoxyphenyl)-piperazine oxalate, m.p. 100°–101° C (decomposition);
1-{3-(m-Fluoroanilino)propyl}-4-(o-methoxyphenyl)-piperazine dihydrochloride, m.p. 227°–228° C (decomposition);
1-{3-(o-Fluoroanilino)propyl}-4-(o-methoxyphenyl)-piperazine dihydrochloride, m.p. 203°–204° C (decomposition);
1-{3-(p-Fluoro-N-propionylanilino)propyl}-4-(o-methoxyphenyl)piperazine, m.p. 113°–113.5° C;
1-{3-[N-(p-Fluorobenzoyl)-p-fluoroaniline]propyl}-4-(o-methoxyphenyl)piperazine dihydrochloride, m.p. 200°–201° C (decomposition);
8-{3-(p-Fluoroanilino)propyl}-1-phenyl-4-oxo-1, 3, 8-triazaspiro[4, 5]decane, m.p. 177°–178° C;
8-{3-(p-Anisidino)propyl}-1-phenyl-4-oxo-1, 3, 8-triazaspiro[4, 5]decane, m.p. 165°–166° C;
1-Phenyl-8-{3-(p-toluidino)propyl}-4-oxo-1, 3, 8-triazaspiro[4, 5]decane, m.p. 194°–195° C;
4-(p-Chlorophenyl)-1-{3-(p-fluoroanilino)propyl}-4-piperidinol, m.p. 144°–144.5° C;
1- 3-{N-Acetyl-p-fluoroanilino)propyl}-4-(p-chlorophenyl)-4-piperidinol, m.p. 151°–151.5° C;
1-{3-(p-Fluoroanilino)propyl}-4-(2-oxo-1-benzimidazonyl)piperidine, m.p. 103°–104° C.

EXAMPLE 2

To a mixture of 4 g of lithium aluminum hydride and 40 ml of tetrahydrofuran was added portionwise 2 g of 8-{2-[N-(p-fluorophenyl)carbamoyl]ethyl}-1-phenyl-4-oxo-1, 3, 8-triazaspiro[4, 5]decane under cooling. Then, the mixture was heated under reflux for 4 hours. To the reaction mixture were gradually added water and benzene under cooling, and the precipitate was filtered off. The organic layer was separated, dried over sodium sulfate evaporated under reduced pressure. The residue was triturated with ether, cooled and filtered to give 8-{3-(p-fluoroanilino)propyl}-1-phenyl-4-oxo-1, 3, 8-triazaspiro[4, 5]decane, m.p. 158°–162° C; recrystallized from benzene, m.p. 177°–178° C.

What is claimed is:
1. An N-(ω-amino)alkylaniline derivative of the formula:

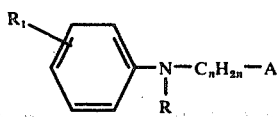

wherein R is hydrogen, $C_1$–$C_7$ alkyl, $C_1$–$C_7$ alkanoyl, benzoyl, halobenzoyl or nicotinoyl, $R_1$ is hydrogen, halogen, $C_1$–$C_7$ alkyl or $C_1$–$C_7$ alkoxy, A is 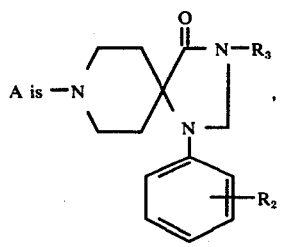

wherein R₂ is hydrogen, halogen, $C_1$–$C_7$ alkyl, $C_1$–$C_7$ alkoxy or trifluoromethyl and R₃ is hydrogen, $C_1$–$C_7$ alkyl or $C_1$–$C_7$ alkanoyl,

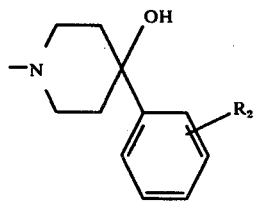

wherein R₂ is as defined above or

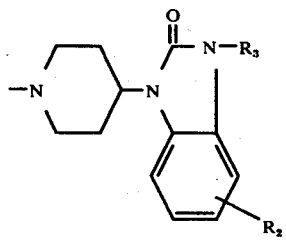

wherein R₂ and R₃ are each as defined above, and $n$ is 2, 3 or 4, and non-toxic pharmaceutically acceptable salts thereof.

2. An (N-(ω-amino)alkylaniline derivative according to claim 1, wherein A is

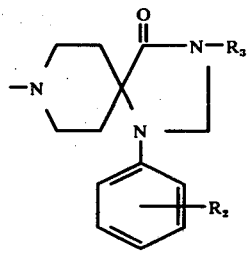

wherein R₂ and R₃ are each as defined in claim 1 and non-toxic pharmaceutically acceptable salts thereof.

3. An N-(ω-amino)alkylaniline derivative according to claim 1, wherein A is

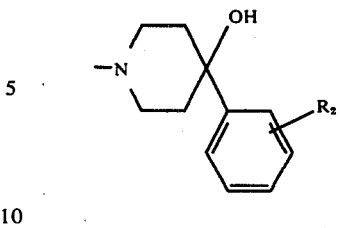

wherein R₂ is as defined in claim 1 and non-toxic pharmaceutically acceptable salts thereof.

4. An N-(ω-amino)alkylaniline derivative according to claim 1, wherein A is

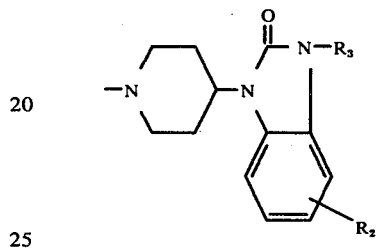

wherein R₂ and R₃ are each as defined in claim 1 and non-toxic pharmaceutically acceptable salts thereof.

5. An N-(ω-amino)alkylaniline derivative according to claim 1, wherein R is hydrogen, R₁ is fluorine, methyl or methoxy at the para-position, $n$ is 3 and A is

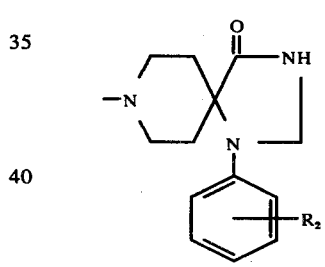

wherein R₂ is $C_1$–$C_3$ alkoxy and non-toxic pharmaceutically acceptable salts thereof.

6. An N-(ω-amino)alkylaniline derivative according to claim 1, wherein R is hydrogen or ethyl and R₁ is fluorine, chlorine, methyl or methoxy, 7. An N-(ω-amino)alkylaniline derivative of the formula:

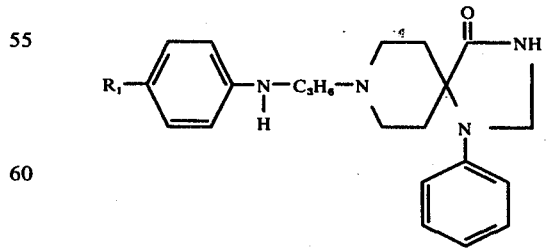

wherein R₁ is fluorine, methyl or methoxy, or non-toxic pharmaceutically acceptable salts thereof.

8. A non-toxic pharmaceutical composition comprising an effective neuroleptic amount of at least one of the N-(ω-amino)alkylaniline derivatives of the formula:

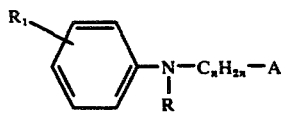

wherein R is hydrogen, $C_1$-$C_7$ alkyl, $C_1$-$C_7$ alkanoyl, benzoyl, halobenzoyl or nicotinoyl, $R_1$ is hydrogen, halogen, $C_1$-$C_7$ alkoxy, A is

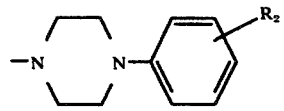

wherein $R_2$ is hydrogen, halogen, $C_1$-$C_7$ alkyl, $C_1$-$C_7$ alkoxy or trifluoromethyl,

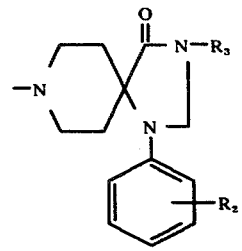

wherein $R_2$ is as defined above and $R_3$ is hydrogen, $C_1$-$C_7$ alkyl or $C_1$-$C_7$ alkanoyl,

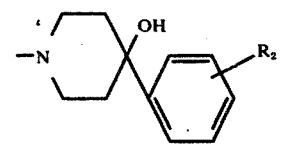

wherein $R_2$ is as defined above or

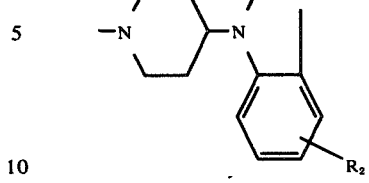

wherein $R_2$ and $R_3$ are each as defined above, and $n$ is 2, 3 or 4, and non-toxic pharmaceutically acceptable salts thereof, and a pharmaceutically acceptable carrier.

9. A non-toxic pharmaceutical composition in accordance with claim 8, wherein the N-(ω-amino)alkylaniline derivative has the formula:

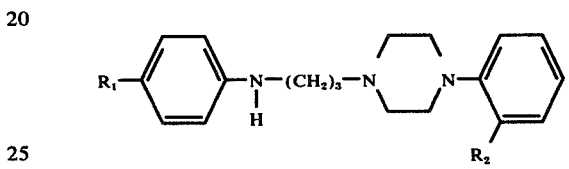

wherein $R_1$ is fluorine, chlorine, methyl or methoxy and $R_2$ is $C_1$-$C_3$ alkoxy, or non-toxic pharmaceutically acceptable acid addition salts thereof.

10. A non-toxic pharmaceutical composition in accordance with claim 8, wherein the N-(ω-amino)alkylaniline derivative has the formula:

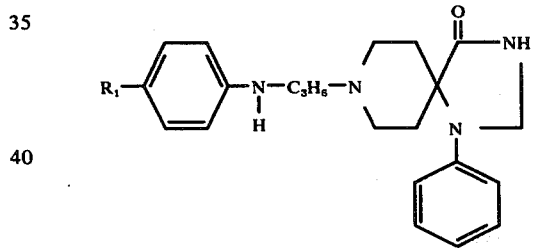

wherein $R_1$ is fluorine, methyl or methoxy, or non-toxic pharmaceutically acceptable salts thereof.

* * * * *